United States Patent  (10) Patent No.: US 9,060,871 B2
Lechmann et al.  (45) Date of Patent: Jun. 23, 2015

(54) TOTAL DISC REPLACEMENT DEVICE

(75) Inventors: Beat Lechmann, Bettlach (CH); Gregor Feigenwinter, Lampenberg (CH); Roger Buerki, Balsthal (CH)

(73) Assignee: DePuy Synthes Products, Inc., Raynham, MA (US)

( * ) Notice: Subject to any disclaimer, the term of this patent is extended or adjusted under 35 U.S.C. 154(b) by 610 days.

(21) Appl. No.: 13/345,161

(22) Filed: Jan. 6, 2012

(65) Prior Publication Data

US 2012/0109315 A1 May 3, 2012

Related U.S. Application Data

(63) Continuation of application No. 11/719,355, filed as application No. PCT/CH2006/000064 on Feb. 1, 2006, now Pat. No. 8,182,536.

(51) Int. Cl.
*A61F 2/44* (2006.01)
*A61F 2/30* (2006.01)

(52) U.S. Cl.
CPC .............. *A61F 2/4425* (2013.01); *A61F 2/442* (2013.01); *A61F 2002/30112* (2013.01); *A61F 2002/30383* (2013.01); *A61F 2002/30448* (2013.01); *A61F 2002/30476* (2013.01); *A61F 2002/30563* (2013.01); *A61F 2002/30574* (2013.01); *A61F 2002/30841* (2013.01); *A61F 2002/30971* (2013.01); *A61F 2002/448* (2013.01); *A61F 2220/0025* (2013.01); *A61F 2220/005* (2013.01); *A61F 2230/0004* (2013.01)

(58) Field of Classification Search
USPC ........................................... 623/17.11–17.16
See application file for complete search history.

(56) References Cited

U.S. PATENT DOCUMENTS

| 4,759,766 | A | * | 7/1988 | Buettner-Janz et al. ... 623/17.15 |
| 5,674,294 | A | | 10/1997 | Bainville et al. |
| 6,063,121 | A | * | 5/2000 | Xavier et al. ............... 623/17.15 |
| 7,637,955 | B2 | | 12/2009 | Marik et al. |
| 7,842,089 | B2 | | 11/2010 | Aaron |
| 8,182,536 | B2 | | 5/2012 | Lechmann et al. |
| 2002/0082701 | A1 | | 6/2002 | Zdeblick et al. |
| 2003/0045939 | A1 | * | 3/2003 | Casutt ........................ 623/17.15 |
| 2003/0135277 | A1 | | 7/2003 | Bryan et al. |

(Continued)

FOREIGN PATENT DOCUMENTS

EP 0950389 10/1999
EP 1214918 6/2002

(Continued)

OTHER PUBLICATIONS

"Titanium Alloys, General Specification Sheet," Matweb, p. 1.

(Continued)

*Primary Examiner* — Mary Hoffman
(74) *Attorney, Agent, or Firm* — Baker & Hostetler LLP

(57) ABSTRACT

An intervertebral implant for implantation between an upper vertebra and a lower vertebra having a central axis. The implant may have a first member with a top surface for contacting at least a portion of the upper vertebra and a bottom surface as well as a second member with a top surface and a bottom surface for contacting at least a portion of the lower vertebra. An elastic spacer may be disposed between the first member and the second member. Constraints may be employed to to limit the amount of lateral movement between the first and second members.

35 Claims, 5 Drawing Sheets

(56) References Cited

U.S. PATENT DOCUMENTS

| | | | |
|---|---|---|---|
| 2004/0073310 A1* | 4/2004 | Moumene et al. | 623/17.13 |
| 2004/0093087 A1* | 5/2004 | Ferree et al. | 623/17.13 |
| 2004/0122518 A1 | 6/2004 | Rhoda | |
| 2004/0193273 A1 | 9/2004 | Huang | |
| 2004/0243240 A1* | 12/2004 | Beaurain et al. | 623/17.14 |
| 2004/0267364 A1* | 12/2004 | Carli et al. | 623/17.14 |
| 2005/0043800 A1* | 2/2005 | Paul et al. | 623/17.15 |
| 2005/0085909 A1* | 4/2005 | Eisermann | 623/17.11 |
| 2005/0154468 A1 | 7/2005 | Rivin | |
| 2005/0165485 A1* | 7/2005 | Trieu | 623/17.13 |
| 2005/0165486 A1* | 7/2005 | Trieu | 623/17.13 |
| 2005/0197705 A1* | 9/2005 | Arnin et al. | 623/17.15 |
| 2006/0052872 A1* | 3/2006 | Studer et al. | 623/17.13 |
| 2006/0190084 A1 | 8/2006 | Doubler et al. | |
| 2006/0229724 A1 | 10/2006 | Lechmann et al. | |
| 2006/0229725 A1 | 10/2006 | Lechmann et al. | |
| 2006/0265068 A1 | 11/2006 | Schwab | |
| 2007/0067036 A1* | 3/2007 | Hudgins et al. | 623/17.13 |
| 2007/0162137 A1* | 7/2007 | Kloss et al. | 623/17.15 |
| 2007/0276495 A1 | 11/2007 | Aaron | |
| 2008/0077244 A1* | 3/2008 | Robinson | 623/17.16 |
| 2008/0133013 A1* | 6/2008 | Duggal et al. | 623/17.16 |
| 2008/0319548 A1* | 12/2008 | Kuras et al. | 623/17.11 |
| 2009/0054989 A1* | 2/2009 | Baumgartner et al. | 623/17.16 |
| 2010/0249936 A1* | 9/2010 | Bertagnoli | 623/17.16 |

FOREIGN PATENT DOCUMENTS

| | | |
|---|---|---|
| EP | 1532950 | 5/2005 |
| FR | 2709949 | 3/1995 |
| FR | 2787021 | 6/2000 |
| FR | 2863868 | 6/2005 |
| WO | 2005/011523 A2 | 2/2005 |
| WO | WO 2005/084385 | 9/2005 |

OTHER PUBLICATIONS

"X10Cr13 Stainless Steel for medical instruments Specification Sheet," Matweb, p. 1.

Meakin, Judith R., et al., "Replacing the nucleus pulposus of the intervertebral disc," Clinical Biomechanics 16 (2001), pp. 560-565.

International Search Report and Written Opinion of the International Searching Authority for the International Application No. PCT/CH2006/000064 dated Oct. 20, 2006.

Young's Modulus (http://wikipedia.com), Jun. 20, 2012.

* cited by examiner

TOTAL DISC REPLACEMENT DEVICE

CROSS REFERENCE TO RELATED APPLICATIONS

This application is a continuation of U.S. patent application Ser. No. 11/719,355, filed Apr. 24, 2009, now U.S. Pat. No. 8,182,536, which is a U.S. National Stage Entry of International Patent Application No. PCT/CH2006/000064, filed Feb. 1, 2006, the entire contents of which are expressly incorporated herein by reference thereto.

FIELD OF INVENTION

The invention relates to a total disc replacement device to be used as a replacement of an intervertebral disc.

DESCRIPTION OF THE PRIOR ART

Currently, degenerated intervertebral discs are treated with fusion cages for arthrodesis and lower grade degenerated discs are replaced by arthroplasty devices. These devices contain mechanical elements including an articulating portion, e.g. a ball-and-socket joint. Such devices shall mimic the segmental motion pattern. However, the natural motion pattern of two adjoining vertebral bodies is very complex due to the surrounding structures which provide mechanical stabilization. Facet joints, remaining ligaments or residual fragments of the annulus fibrosis are part of the segmental stabilization.

For the currently available Total Disc Replacement Implants the surgeon shall remove the Anterior Longitudinal Ligament (ALL) and the Posterior Longitudinal Ligament (PLL) in order to release the motion segment completely. After such a surgical intervention, the total disc replacement implant can provide the function as a prosthesis.

An artificial disc implant is known from US-A 2002/0082701 to Zdeblick. This U.S. patent application publication discloses an artificial disc implant which is provided with an upper and a lower shell as well as an elastic spacer there between. Furthermore, the surfaces of the shells which are facing each other are provided with constraint means by means of which the motion of the shells relative to one another is limited. Nevertheless, the disclosed configuration of the constraint means does not allow a rigid limitation of the lateral motion of the shells relative to one another until the implant is completely compressed.

An intervertebral disc prosthesis is known from EP-A 1 532 950 to Filippi. This known prosthesis is provided with two apposition members separated by a lens shaped core. The core has two opposite spherical articulating surfaces which slidably engage corresponding recesses in the intermediate surfaces of the apposition members. Furthermore, the core is provided with bores penetrating into the core at the vertices of the articulating surfaces wherein each pin attached to the intermediate surface is receivable in a laterally displaceable manner. The pin being laterally displaceably arranged in the bore together with the lateral wall of the bore serve as constraint means but since the second constraint means are configured at the elastic core said constraint means do not allow to rigidly limit the lateral motion and the pivoting of the two apposition members relative to one another within a desired range.

An implantable intervertebral disc prosthesis having a pair of opposed shell like apposition members and a resilient central body disposed between these apposition members is known from US-A 2003/0135277 to Bryan. This known disc prosthesis comprises constraint means which limit the range of lateral bending and lateral translation of the two apposition members relative to each other and consequently of the adjacent vertebral bodies relative to each other. Disadvantageously, the inner constraint means are arranged at the resilient central body and do therefore not allow a rigid limitation of the range of motion.

Accordingly, it is the principal object of the present invention to provide a total disc replacement device which permits a dampened motion of the apposition members relative to each other until a rigid limitation of the range of at least the lateral motion is reached.

According to the invention the above object is achieved through a total disc replacement device with a central axis and comprising a first apposition member with an apposition surface and an intermediate surface both being arranged transversely to said central axis and a second apposition member with an apposition surface and an intermediate surface; said intermediate surfaces of said first and second apposition members facing each other. Furthermore, an elastic spacer disposed between said intermediate surfaces of said first and second apposition members is provided. Said intermediate surface of said first apposition member is provided with first rigid constraint means and said intermediate surface of said second apposition member is provided with second rigid constraint means interfering with said first constraint means and being configured such that a gap with a width W>0 is provided at least transversely to the central axis between said first and second constraint means in the unloaded state of the total disc replacement device.

The device according to the invention as such offers the advantages that:

(a) the translation in lateral or in antero-posterior direction of the adjacent vertebral bodies relative to each other is limited, particularly in case of extreme bending of the vertebra;

(b) the facet joints are protected in case of lateral or antero-posterior movement as well as in case of axial rotation of the spinal segment of the adjacent vertebral bodies;

(c) the motion of the adjacent vertebral bodies is dampened due to the elastic property of the spacer between the rigid metallic apposition members;

(d) the more the elastic spacer is compressed, the more it acts as a soft break;

(e) the total disc replacement device is apt to restore the lordotic curve and distract the segment due to the combined rigid-elastic structure of the device;

(f) a superposed motion of the total disc replacement device is allowed similar to the natural intervertebral disc.

In a preferred embodiment said spacer extends into the gap between the first and second constraint means, thus allowing the advantage of a damping effect in case of relative motion of the first and second apposition members.

In a further embodiment said spacer completely fills the gap.

In yet a further embodiment said first and second constraint means are configured to limit the displacability of said first and second apposition member relative to one another at least transversely to said central axis, thus allowing a rigid limitation of the range of motion of said first and second apposition member as such of the adjoining vertebral relative to one another.

In another embodiment said elastic spacer is made of a material A having a Young's modulus $Y_A$ and said first and second apposition members are made of a material B having a Young's modulus $Y_B$ and wherein $Y_A$ is between 4% and 66% of $Y_B$.

In a further embodiment the Young's modulus Y A of said material A is smaller than 60 GPa.

In yet another embodiment the Young's modulus $Y_A$ of said material A is between 15 GPa and 60 GPa.

In still a further embodiment the Young's modulus $Y_B$ of said material B is greater than 90 GPa.

In again another embodiment the Young's modulus $Y_B$ of said material B is between 90 GPa and 350 GPa.

In a further embodiment said elastic spacer is made of a composite material or a material combination, thus allowing the advantage that e.g. two different polymeric materials permit a more sophisticated damping effect.

In yet a further embodiment the first and second apposition plate are made from a metal, preferably titan or a titan alloy.

In another embodiment the elastic spacer is made from a plastic.

In still a further embodiment said first or second constraint means comprises a projection protruding over the respective intermediate surface and the other of said first and second constraint means comprises at least one limiting wall axially overlapping said projection.

In yet another embodiment said at least one limiting wall is configured to permit a displacement of said projection within an area orthogonal to said central axis.

In a further embodiment said first and second constraint means are located centrally on said intermediate surfaces.

In yet a further embodiment the constraint means are configured in a manner that:

the projection has a diameter between 1.5 mm and 18 mm;

the at least one limiting wall limits the motion of the projection within a length l between 2 mm and 24 mm measured parallel to the first transverse axis which preferably coincides or is parallel to the lateral axis of the vertebral bodies; and within a width b between 1.8 mm and 32 mm measured parallel to the second transverse axis which preferably coincides or is parallel with the antero-posterior axis of the vertebral bodies.

In a further embodiment said gap has a width W1 parallel to a first transverse axis being orthogonal to the central axis and a width W2≠W1 parallel to a second transverse axis being orthogonal to the central axis and the first transverse axis. This design allows the advantage that the motions of the first and second apposition plate relative to one another in the antero-posterior direction and in the lateral direction are differently limited through the constraint means.

In another embodiment said first constraint means is configured as a central pin protruding over said intermediate surface of said first apposition member.

In yet a further embodiment said central pin has a convex, preferably spherical tip allowing a tilting motion between the first and second apposition member when the elastic spacer is compressed parallel to the central axis until the intermediate surface of the second apposition member abuts the tip of the central pin. The advantage of this design is a limitation of the elastic compressibility of the implant parallel to the central axis.

In still another embodiment said second constraint means are formed by at least one curved protrusion projecting out over said intermediate surface of said second apposition member, thus allowing the advantage of a configuration which provides more constrain, i.e. less translation in antero-posterior direction whereas it allows more motion laterally. This configuration has its advantages by the treatment of Spondylo-listhesis grade 1 according to Meyerding. This slight misalignment can be treated with total disc replacement implant without additional stabilization.

In a further embodiment said at least one curved protrusion is provided with a concavely curved interior wall facing the central axis which forms a boundary line of the cross-sectional area of the at least one protrusion orthogonal to the central axis, said boundary line being at least a section of a circle, an oval or an ellipse.

In another embodiment said second constraint means comprises two curved protrusions having cross-sectional areas orthogonal to the central axis that are centrally symmetric to the point of intersection where the central axis cuts the intermediate surface of said second apposition member.

In yet a further embodiment said first and second constraint means comprise a keel and a groove being in tiltable engagement.

In another embodiment said first and second constraint means comprise a spherical segment and a corresponding spherical recess.

In a further embodiment said total disc replacement device additionally comprises form fitting retention means disposed between said first and second apposition members and said elastic spacer, thus allowing the advantage of a rigid bonding of the elastic spacer to the first and second apposition plates.

In another embodiment said retention means comprise a peripheral frame projecting out over said intermediate surfaces of said first and second apposition members, said peripheral frame being provided with an undercut and being encompassed by said elastic spacer.

In still a further embodiment said intermediate surfaces of said first and second apposition members contact said elastic spacer over the entire area of said intermediate surfaces, and said first and second apposition members and said elastic spacer form a compact body with planar or convex lateral surfaces. This design allows the advantage of preventing fluid from the human body flowing into the implant and destroy the implant.

In yet a further embodiment said first and second apposition members have an elongated shape with a major axis and a transverse minor axis when viewed parallel to said central axis.

In another embodiment said first and second apposition members have a length L measured parallel to said major axis and a maximum width B measured parallel to said transverse minor axis, whereby the ratio of the length L to the maximum width B is between 3:1 and 5:1. This embodiment offers the advantage that it is only necessary to clear a narrow access path such permitting an extraforaminal approach to the intervertebral disc space.

In a further embodiment said central axis, major axis and transverse minor axis intersect each other and said central axis and transverse minor axis define a middle plane and whereby said first and second apposition members have a cross-sectional area orthogonal to said central axis which is essentially oval or elliptical and comprises at least two concavities lying on different sides of said middle plane and on the same side of said major axis. The advantages of this design essentially are:

unnecessary material on the first and second apposition plates (bone contact plates) is removed in order to give special attention to the fact that the bony end plates of the vertebral bodies change their shape at the location where the prosthesis is situated during their degeneration, i.e. they become more undulated over time; and possible osteophytes on the posterior periphery of the vertebral endplates which the surgeon decides not to remove are taken into consideration, i.e. the intervertebral prosthesis can be positioned easier because the prosthesis can be manipulated around the undulations.

In yet another embodiment said cross-sectional area of said first and second apposition members is kidney shaped with an enlargement arranged essentially symmetrical to said middle plane.

In still a further embodiment said at least two concavities have an essentially semi-elliptical or semi-oval shape.

In another embodiment said at least two concavities are disposed essentially symmetrical to said middle plane.

In yet a further embodiment said first and second apposition members have a length L measured parallel to said major axis and wherein each of said at least two concavities has a width W measured parallel to said major axis, said width W amounting to between 15% and 35% of said length L.

In still another embodiment said first and second apposition members have a maximum width B measured parallel to said transverse minor axis and wherein each of said at least two concavities has a depth T measured parallel to said transverse minor axis, said depth T amounting to between 3% and 25% of said maximum width B.

In a further embodiment said cross-sectional area of said first and second apposition members has an essentially elliptical periphery with a smaller radius of curvature at the first subsidiary vertex than at the second subsidiary vertex of said periphery.

In yet another embodiment said first subsidiary vertex is on the same side of said major axis as said at least two concavities.

In still a further embodiment said spacer completely fills the gap.

In another embodiment said first and second constraint means are configured to permit a relative displacement of said first and second apposition members parallel to said central axis.

In yet another embodiment said first and second constraint means interfere mechanically.

Brief Description of the Surgical Implantation Methods:
Variant I: (FIGS. 1-3)

This type of total disc replacement device is implanted from anterior, anterolateral or lateral applying known surgical techniques.

Variant II: (FIGS. 4 and 5)

This type of total disc replacement device is implanted as an interbody fusion cage. Since one crucial aspect of the implantation of a total disc replacement device is to keep the anterior longitudinal ligament (ALL) and the posterior longitudinal ligament (PLL) intact, preferably posteriorly inserted total disc replacement devices are designed which are—due to the small access to the intervertebral space—applied in pairs. The above mentioned ligaments and the residual elements of the annulus fibrosis provide segmental stability to the functional spine unit or spinal motion segment. The two devices are inserted through a posterior median incision whereby the devices have to pass the spinal canal.

Variant III: (FIGS. 6-8)

The device is inserted into the intervertebral space by means of an extraforaminal access.

A BRIEF DESCRIPTION OF THE DRAWINGS

Further objects and advantages of the invention will become apparent from the following description when read with reference to the accompanying drawings which illustrate several embodiments of the invention. In the drawings.

DETAILED DESCRIPTION

Figure 1:
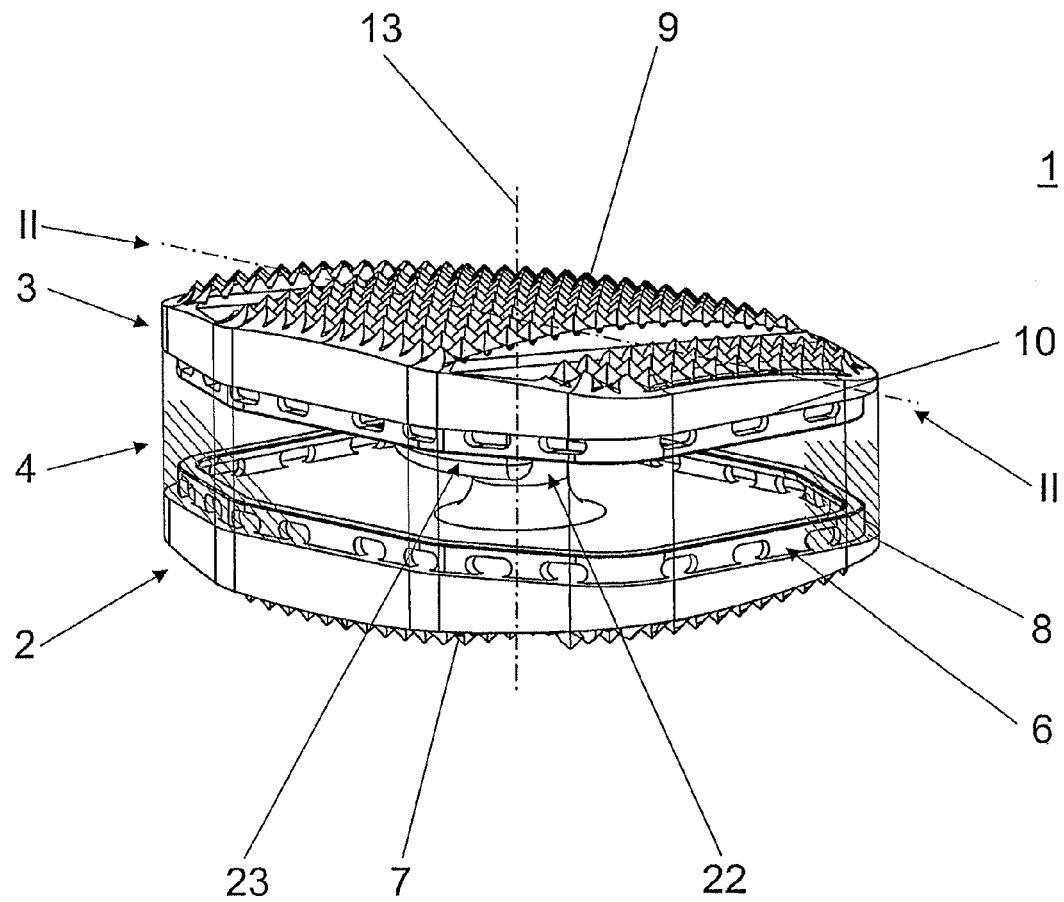
FIG. 1 shows a perspective view of an embodiment of a total disc replacement device according to the present invention.

In FIG. 1 an embodiment of a total disc replacement device 1 according to the invention is represented which comprises a first and a second plate-shaped apposition member 2,3 and an elastic spacer 4 disposed between the first and second apposition member 2,3. The first and second apposition members 2,3 and the elastic spacer 4 are being cut by a central axis 13 extending along the longitudinal axis of the vertebra. The first and second apposition members 2,3 each comprise an apposition surface 7,9 and an intermediate 8,10 whereby said apposition surfaces 7,9 are apt to abut the end plates of the adjoining vertebral bodies and whereby said intermediate surfaces 8,10 are arranged facing each other. Furthermore, the elastic spacer 4 comprises a first and a second surface which are essentially parallel and abut an intermediate surface 8,10 of the apposition members 2,3 each. In order to limit the mutual translation of the apposition members 2,3 transverse to the central axis 13 the intermediate surfaces 8,10 of the first and second apposition members 2,3 are provided with first and second constraint means 22,23.

The first constraint means 22 is provided at the intermediate surface 8 of said first apposition member 2 while the second constraint means 23 is provided at the intermediate surface 10 of said second apposition member 3 in a manner that said second rigid constraint means 23 interfere with said first constraint means 22 and being configured such that a gap 21 is provided transversely as well as parallel to the central axis 13 between said first and second constraint means 22,23 in the unloaded state of the total disc replacement device 1. The elastic spacer 4 completely fills the gap 21 such allowing a damping effect in case of relative motion of said first and second apposition member 2,3 in three orthogonal directions.

Figure 2:
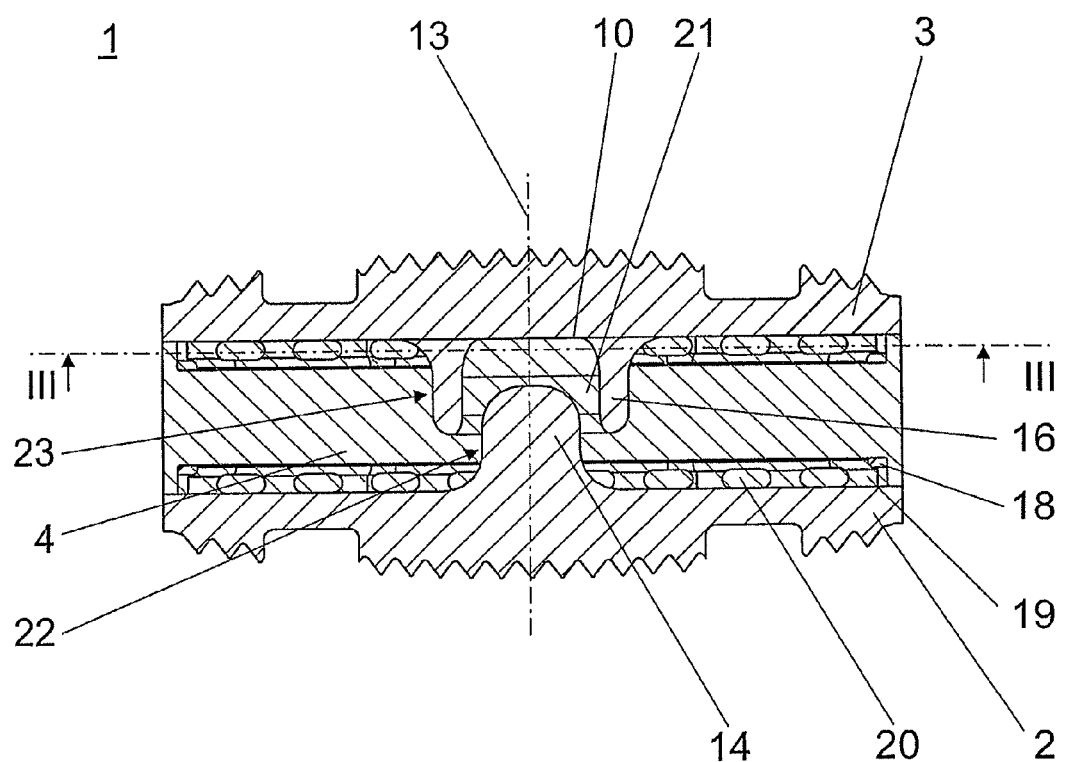
FIG. 2 shows a cross-section through the device of FIG. 1 along the line II-II.
Figure 3:
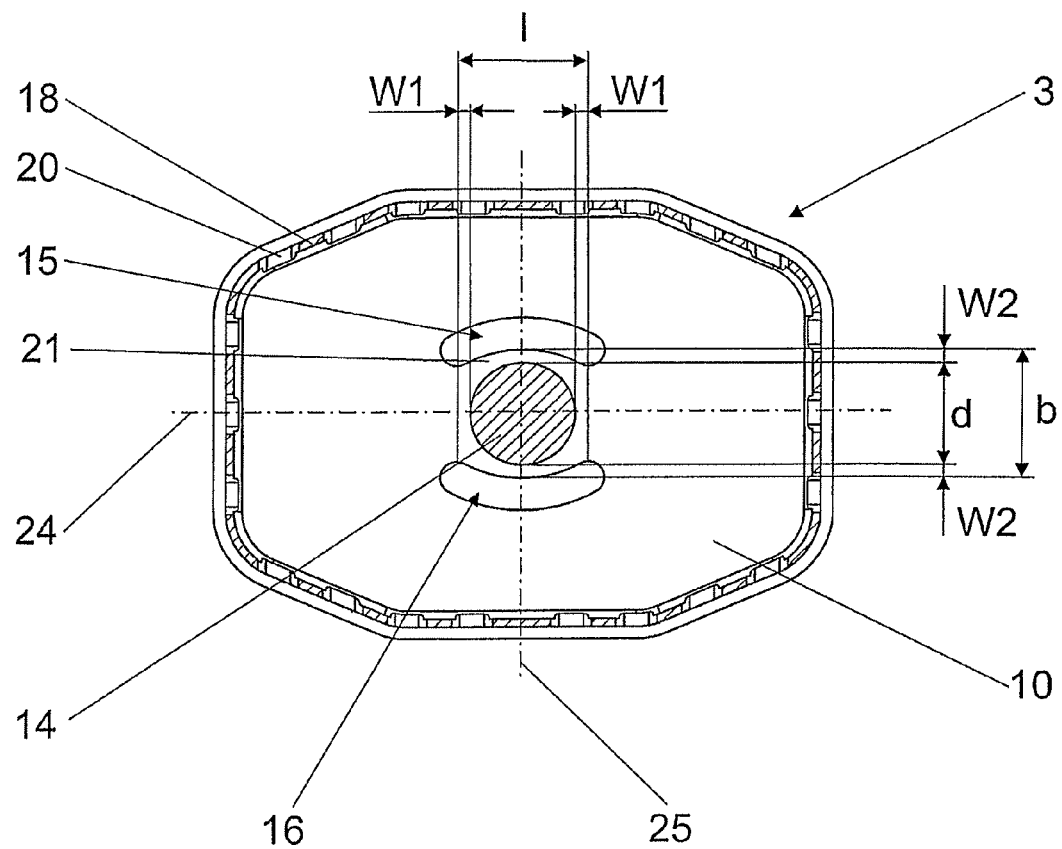
FIG. 3 shows a cross-section through the device of FIGS. 1 and 2 along the line III-III in FIG. 2.

As shown in FIGS. 2 and 3 the first constraint means 22 are configured as a projection having the form of a central pin 14 protruding over the intermediate surface 8 of the first apposition member 2 while the second constraint means 23 comprise first and second curved protrusions 15,16 at the intermediate surface 10 of the second apposition member 3, said first and second curved protrusions 15,16 enclosing a recess partially surrounding said central pin 14 such forming a rigid spatial limitation. The central pivot pin 14 has a certain range of motion parallel and transverse to the central axis 13 within said spatial limitation.

As shown in FIG. 3 said gap 21 has a width W1 parallel to a first transverse axis 24 being orthogonal to the central axis 13 and a width $W2 \neq W1$ parallel to a second transverse axis 25 being orthogonal to the central axis 13 and the first transverse axis 24 such allowing relative motions of the first and second apposition member 2,3 being differently in the antero-posterior direction and in the lateral direction.

Furthermore, said central pin 14 has a convex tip further allowing a tilting motion between said first and second apposition member 2,3 when the elastic spacer 4 is compressed parallel to the central axis 13 until the intermediate surface 10 of the second apposition member 3 abuts the tip of the central pin 14.

Said first and second curved protrusion 15,16 being provided with a concavely curved interior wall facing the central axis 13 which forms a boundary line of the cross-sectional area of each of said first and second protrusion 15,16 orthogonal to the central axis 13, said boundary line being a section of an ellipse. Furthermore, said first and second curved protrusions 15,16 have a cross-sectional area orthogonal to the central axis 13 such that the two crosssectional areas are centrally symmetric to the point of intersection where the central axis 13 cuts the intermediate surface 10 of said second apposition member (3).

Furthermore, said total disc replacement device 1 comprises form fitting retention means 6 disposed between each of said first and second apposition members 2,3 and said elastic spacer 6 such allowing a firm bonding of the elastic spacer 4 to the first and second apposition plates 2,3. Said retention means 6 consist of a peripheral frame 18 disposed near the periphery of the cross-sectional areas orthogonal to said central axis 13 of said first and second apposition member 2,3 and projecting out over said intermediate surfaces 8,10 of said first and second apposition members 2,3. An undercut 19 is provided at said peripheral frame 18 which is encompassed by said elastic spacer 4. Furthermore, said peripheral frame 18 is provided with perforations 20 penetrating the peripheral frame 18 transversely to said central axis 13 and being filled with the material of said elastic spacer 4.

Figure 4:
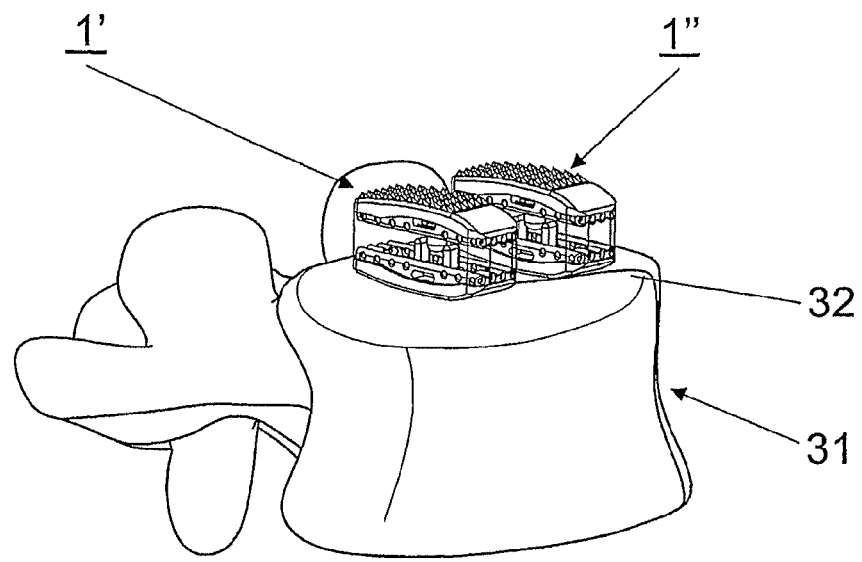
FIG. 4 shows a perspective view of a vertebral body whereby the intervertebral space adjoining its cover plate is being provided with two other embodiments of total disc replacement devices according to the present invention.
Figure 5:
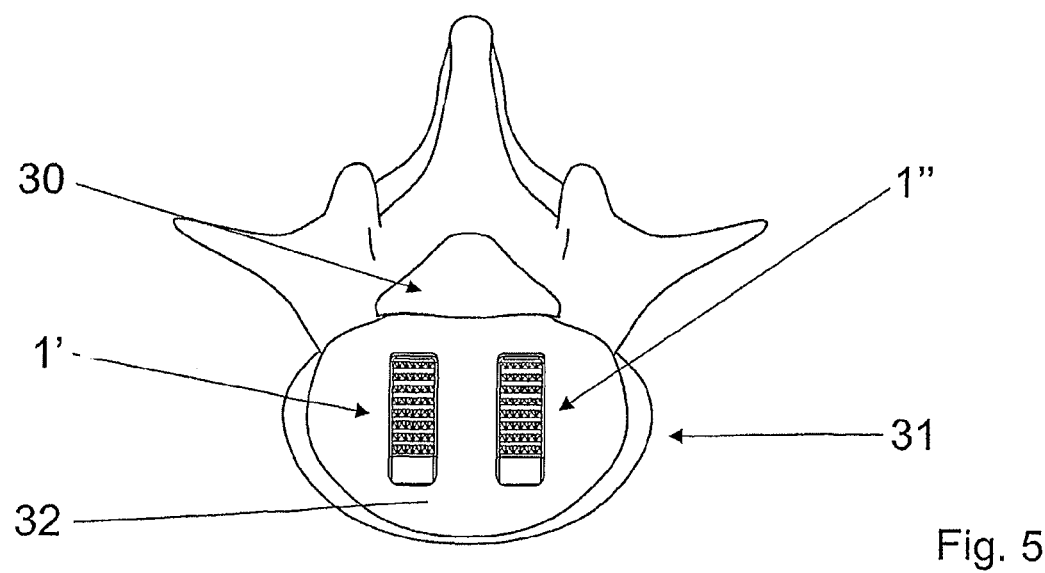
FIG. 5 shows a top view on the vertebral body of FIG. 4.

FIGS. 4 and 5 show posteriorly inserted total disc replacement devices 1',1" that are both provided with constraint means 22,23 and form fitting retaining means 6 as illustrated in FIGS. 1-3. The total disc replacement devices 1',1" therefore essentially differ only in their lateral and antero-posterior dimensions from the total disc replacement device 1 shown in FIGS. 1-3. Due to the small access to the intervertebral space these lateral and antero-lateral dimensions must be selected such that the total disc replacement devices 1',1"' must be implanted in pairs. Since one crucial aspect to apply the surgical techniques as described above are the intact anterior longitudinal ligaments and the posterior longitudinal ligaments. These ligaments and the residual elements of the annulus fibrosis provide segmental stability to the functional spine unit or spinal motion segment. From posterior lumbar interbody fusion surgery it is known that all these structures remain intact. Therefore, posteriorly inserted total disc replacement devices 1',1''' can be designed and applied with motion preserving elements, i.e. an elastic spacer 4 as well. Said pair of total disc replacement devices 1',1" are inserted through the posterior median incision as described above under variant 2. The devices must be passed through the spinal canal during insertion. Furthermore, the elastic spacer 4 allows even a slight malpositioning of the total disc replacement devices 1',1" since there are no predefined centers of rotation as being provided by implants having e.g. a spherical ball-and-socket joint.

Figure 6:
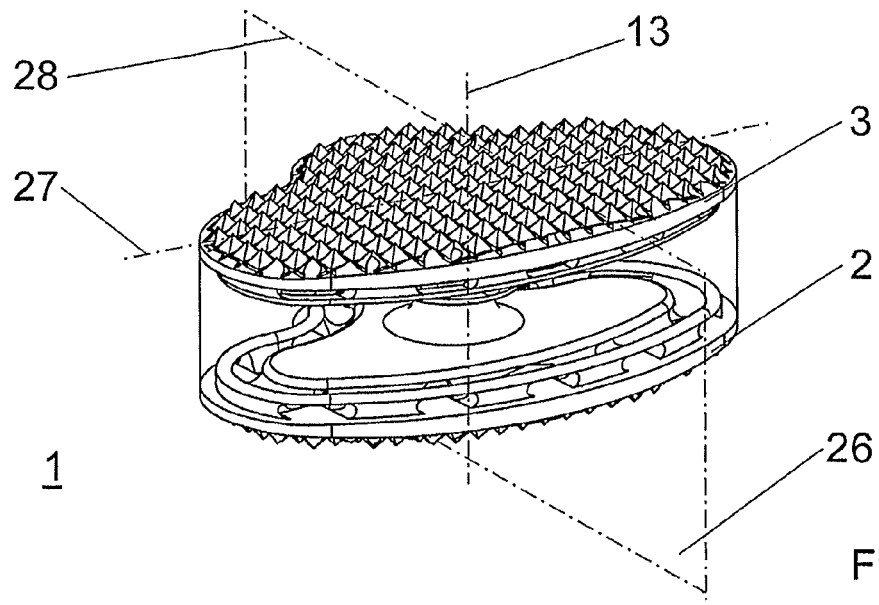
FIG. 6 shows a perspective view of another embodiment of a total disc replacement device according to the present invention.
Figure 7:
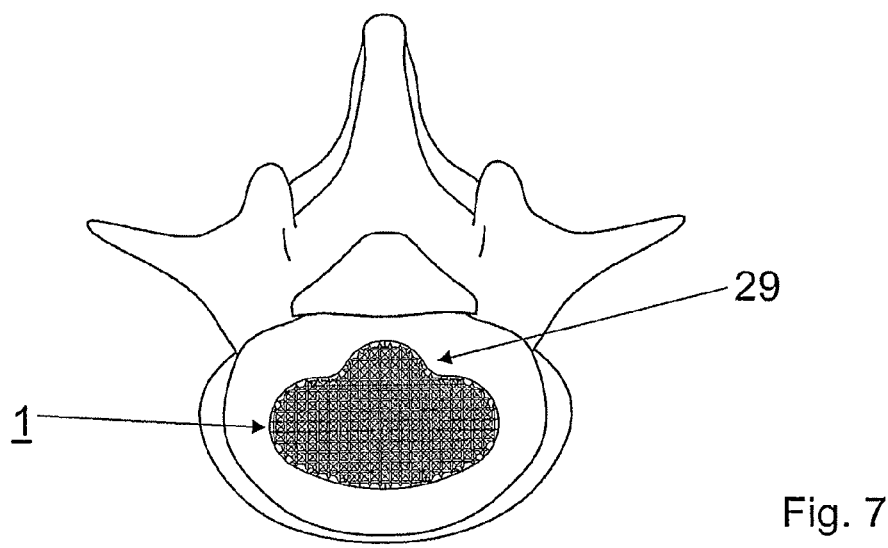
FIG. 7 shows a top view of a vertebral body whereby the intervertebral space adjoining its cover plate is being provided with the device of FIG. 6.
Figure 8:
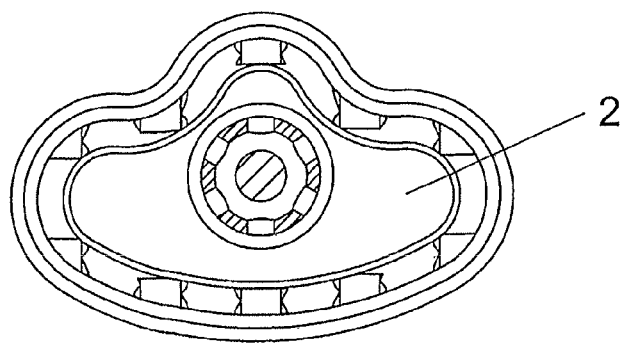
FIG. 8 shows a top view on the second apposition member of the device of FIGS. 6 and 7.

The embodiment shown in FIGS. 6-8 differs from the embodiment shown in FIGS. 1-3 only in the shape of the cross-sectional area orthogonal to said central axis 13 of the first and second apposition member 2,3. FIGS. 6-8 illustrate an embodiment also comprising a first apposition member 2, a second apposition member 3 and an elastic spacer 4 therebetween. Opposite said elastic spacer 4 the first and second apposition member 2,3 comprise a first apposition surface 7, respectively a second apposition surface 9, whereby said second apposition surface 9 is configured for abutting the base plate of a first intervertebral body contacting the total disc replacement device 1 on top and said first apposition surface 7 is configured for abutting the cover plate of a second intervertebral body contacting the total disc replacement device 1 at the bottom.

Each of the first and second apposition surfaces 7, 9 is disposed transversely to the central axis 13. When viewed parallel to said central axis 13 said first and second apposition members 2,3 have an elongated shape with a major axis 27 and a transverse minor axis 28, whereby said central axis 13, major axis 27 and transverse minor axis 28 intersect each other. Said central axis 13 and said transverse minor axis 28 further define a middle plane 26. Furthermore, said first and second apposition member 2,3 have a cross-sectional area orthogonal to said central axis 13 which is essentially elliptical and comprises two concavities lying on different sides of said middle plane 26 and on the same side of said major axis 27.

The two concavities are disposed symmetrically to said middle plane 26 such that one of said two concavities is arranged in a first quadrant of a circle the centre of which coincides with the point of intersection of the major axis 27, the transverse minor axis 28 and the central axis 13 and the circumference of which is tangent to the periphery of said cross-sectional area at the principal vertices. The second of said two concavities is arranged in a clockwise succeeding, second quadrant of said circle. Furthermore, the two concavities have an essentially semielliptical shape and have a depth T measured parallel to said transverse minor axis 28 amounting to about 5% of the maximum width B of said first and second apposition members 2,3.

What is claimed is:

1. An intervertebral implant for implantation between an upper vertebra and a lower vertebra, the intervertebral implant comprising:
    a first member including a top surface configured to face at least a portion of the upper vertebra when the intervertebral implant is implanted between the upper and lower vertebrae, the first member further including a bottom surface and a first peripheral edge;
    a second member having a top surface spaced from the bottom surface of the first member in a first direction, the second member further including a bottom surface and a second peripheral edge, the bottom surface configured to face at least a portion of the lower vertebra when the intervertebral implant is implanted between the upper and lower vertebrae; and
    a single, continuous elastomeric material disposed between said bottom surface of said first member and said top surface of said second member,
    wherein one of said bottom surface of said first member and said top surface of said second member is provided with a first constraint, and the other of said bottom surface of said first member and said top surface of said second member is provided with a second constraint and the intervertebral implant is configured to be assembled such that:
    a) the first constraint is at least partially surrounded by the second constraint thereby allowing a first maximum amount of relative movement of the first and second members in a second direction, and a second maximum amount of relative movement in a third direction that is different than the second direction, the first maximum amount different than the second maximum amount, and both the second and third direction being transverse to the first direction; and b) the elastomeric material is disposed between the bottom surface of the first member and the top surface of the second member both at a first location between the first constraint and the second constraint, and at a second location not between the first constraint and the second constraint.

2. The intervertebral implant of claim 1, wherein said first and second constraints are configured such that the second maximum amount of relative movement allowed in the third direction between said first and second constraints is between about 2 mm and about 24 mm.

3. The intervertebral implant of claim 1, wherein said first member defines a first peripheral edge, said second member defines a second peripheral edge, and said elastomeric material is a single continuous material that extends from and between: 1) the first and second peripheral edges, and 2) the bottom surface of the first member and the top surface of the second member.

4. The intervertebral implant of claim 1, wherein said first constraint is located centrally on one of said bottom surface of said first member and said top surface of said second member and said second constraint is located centrally on the other of said bottom surface of said first member and said top surface of said second member.

5. The intervertebral implant of claim 1, wherein said elastomeric material is made of a material A having a Young's modulus $Y_A$ and said first and second members are made of a material B having a Young's modulus $Y_B$ and wherein $Y_A$ is between 4% and 66% of $Y_B$.

6. The intervertebral implant of claim 5, wherein the Young's modulus $Y_A$ of said material A is smaller than 60 GPa.

7. The intervertebral implant of claim 6, wherein the Young's modulus $Y_A$ of said material A is between 15 GPa and 60 GPa.

8. The intervertebral implant of claim 5, wherein the Young's modulus $Y_B$ of said material B is greater than 90 GPa.

9. The intervertebral implant of claim 8, wherein the Young's modulus $Y_B$ of said material B is between 90 GPa and 350 GPa.

10. The intervertebral implant of claim 1, further comprising a form fitting retention member disposed between said first member and said elastomeric material, and disposed between said second member and said elastomeric material, said retention member comprising a peripheral frame extending from said bottom surface of said first member and said top surface of said second member, said peripheral frame being sized and configured to secure said elastomeric material in-between said first and second members.

11. The intervertebral implant of claim 10, wherein said peripheral frame includes an undercut, the undercut being sized and configured to be encompassed by said elastomeric material.

12. The intervertebral implant of claim 1, wherein the intervertebral implant is configured to be assembled such that a gap with a width greater than zero is provided at least transversely to said first direction between said first and second constraints in an unloaded state.

13. The intervertebral implant of claim 12, wherein said elastomeric material extends into said gap.

14. The intervertebral implant of claim 12, wherein said gap has a width W1 parallel to the second direction, the second direction being perpendicular to the first direction, and a width W2 parallel to the third direction, the third direction being perpendicular to both the first direction and the second direction, said width W1 being different from said width W2.

15. The intervertebral implant of claim 1, wherein the first direction is a cranial-caudal direction, the second direction is an antero-posterior direction and the third direction is a lateral direction.

16. The intervertebral implant of claim 1, wherein the first constraint is configured as a central pin having a convex tip configured to permit a tilting motion between said first and second members, the central pin defining a maximum width as measured in a direction perpendicular to the first direction, the second constraint is configured as at least two separate curved concave protrusions, the at least two separate concave protrusions defining a plurality of openings, each of the plurality of openings being smaller than the maximum width of the central pin, and the intervertebral implant is configured to be assembled such that the central pin is at least partially surrounded by the at least two separate concave protrusions thereby allowing the first maximum amount of relative movement of the first and second members in the second direction to differ from the second maximum amount of relative movement in the third direction, both the second and third direction being transverse to the first direction.

17. The intervertebral implant of claim 1, wherein the second constraint includes an inner side wall that faces the first constraint when the intervertebral implant is assembled such that the first constraint is at least partially surrounded by the second constraint, the second constraint including an outer side wall opposite the inner side wall, the first location positioned closer to the inner side wall than the first location is positioned to the outer side wall, and the second location positioned closer to the outer side wall than the second location is positioned to the inner side wall.

18. An intervertebral implant for implantation between an upper vertebra and a lower vertebra, the intervertebral implant comprising:

a first member including a top surface configured to face at least a portion of the upper vertebra when the intervertebral implant is implanted between the upper and lower vertebrae, the first member further including a bottom surface;

a second member including a top surface spaced from the bottom surface of the first member in a first direction, the second member further including a bottom surface configured to face at least a portion of the lower vertebra when the intervertebral implant is implanted between the upper and lower vertebrae;

an elastomeric material disposed between said bottom surface of said first member and said top surface of said second member;

wherein one of said bottom surface of said first member and said top surface of said second member includes a central pin having a maximum width measured in a direction perpendicular to the first direction, the central pin being monolithic with the first member, and the other of said bottom surface of said first member and said top surface of said second member includes a plurality of separate curved concave protrusions defining a plurality of openings, each of the plurality of openings being smaller than the maximum width of the central pin.

19. The intervertebral implant of claim 18, wherein said first member defines a first peripheral edge, said second member defines a second peripheral edge, and said elastomeric material is a single continuous material that extends from and between: 1) the first and second peripheral edges, and 2) the bottom surface of the first member and the top surface of the second member.

20. The intervertebral implant of claim 18, further comprising a retention member disposed between said first member and said elastomeric material, and disposed between said second member and said elastomeric material, said retention member comprising a peripheral frame extending from said bottom surface of said first member and said top surface of said second member, said peripheral frame being sized and configured to secure said elastomeric material in-between said first and second members.

21. The intervertebral implant of claim 20, wherein said peripheral frame includes an undercut, the undercut being sized and configured to be encompassed by said elastomeric material.

22. The intervertebral implant of claim 18, wherein the central pin has a convex tip for permitting a tilting motion between said first and second members.

23. The intervertebral implant of claim 18, wherein the intervertebral implant is configured to be assembled such that the central pin is at least partially surrounded by the plurality of concave protrusions and in an unloaded state a gap is defined between the central pin and the plurality of separate curved concave protrusions thereby allowing: 1) a first maximum amount of relative movement of the first and second members in a second direction that is perpendicular to the first direction, and a second maximum amount of relative movement in a third direction that is perpendicular to both the first and second directions, and the first maximum amount is different than the second maximum amount.

24. The intervertebral implant of claim 23, wherein said central pin and each of said plurality of separate curved concave protrusions are configured such that the second maximum amount of relative movement allowed in the third direction between said first and second members is between about 2 mm and about 24 mm.

25. The intervertebral implant of claim 18, wherein each of said plurality of separate curved concave portions is provided with a concavely curved interior wall that faces the central pin.

26. An intervertebral implant for implantation between an upper vertebra and a lower vertebra, the intervertebral implant comprising:
a first member with a top surface configured to face at least a portion of the upper vertebra when the intervertebral implant is implanted between the upper and lower vertebrae, the first member further including a bottom surface;
a second member with a top surface and a bottom surface, the bottom surface configured to face at least a portion of the lower vertebra when the intervertebral implant is implanted between the upper and lower vertebrae;
an elastomeric material disposed between said bottom surface of said first member and said top surface of said second member; and
a retention assembly disposed between said first member and said elastomeric material, and further disposed between said second member and said elastomeric material, said retention assembly including a first peripheral frame that extends from said bottom surface of said first member and a second peripheral frame that extends from said top surface of said second member, each of said first and second peripheral frames further defining a plurality of holes such that the elastomeric material fills the plurality of holes to connect the elastomeric material to the retention assembly;
wherein one of said bottom surface of said first member and said top surface of said second member is provided with a first constraint and the other of said bottom surface of said first member and said top surface of said second member is provided with a second constraint, said first and second constraints being configured to limit relative movement between said first and second members;
wherein when the intervertebral implant is in an assembled configuration such that the elastomeric material fills the plurality of holes of the first and second peripheral frames, said first and second constraints are configured such that a gap with a width greater than zero is provided between said first and second constraints.

27. The intervertebral implant of claim 26, wherein said first and second constraints are configured to limit relative movement between said first and second members to an amount between about 2 mm and about 24 mm.

28. The intervertebral implant of claim 26, wherein said first member defines a first peripheral edge, said second member defines a second peripheral edge, and said elastomeric material is a single continuous material that extends from and between: 1) the first and second peripheral edges, and 2) the bottom surface of the first member and the top surface of the second member.

29. The intervertebral implant of claim 26, wherein said first and second peripheral frames are each provided with an undercut that is encompassed by said elastomeric material.

30. The intervertebral implant of claim 26, wherein said bottom surface of said first member and said top surface of said second member contact said elastomeric material over the entire area of said bottom surface of said first member and said top surface of said second member, and wherein said first and said second members and said elastomeric material form a compact body with planar or convex lateral surfaces.

31. The intervertebral implant of claim 26, wherein said elastomeric material extends into said gap.

32. The intervertebral implant of claim 26, wherein said second constraint includes first and second curved protrusions.

33. The intervertebral implant of claim 32, wherein said first and second curved protrusions each include a concavely curved interior wall face.

34. The intervertebral implant of claim 26, wherein said first constraint is configured as a central pin protruding from one of said bottom surface of said first member and said top surface of said second member, said central pin having a convex tip for permitting a tilting motion between said first and second members.

35. The intervertebral implant of claim 34, wherein the central pin has a width and the second constraint comprises two separate curved concave protrusions surrounding the central pin, the two separate concave protrusions defining two opposite openings, the opening being smaller than the width of the central pin, wherein the two separate concave portions limit relative motion of the first and second members but permit relative movement of the first and second member in a first direction to differ from an amount of relative movement in a second direction that is different than the first direction.

* * * * *